United States Patent [19]

Daubach et al.

[11] 4,218,218
[45] Aug. 19, 1980

[54] STABLE FINELY DISPERSED AQUEOUS FORMULATIONS OF DISPERSE DYES AND OPTICAL BRIGHTENERS, AND THEIR USE

[75] Inventors: Ewald Daubach; Manfred Herrmann; Knut Oppenlaender, all of Ludwigshafen; Karl Stork, Lampertheim, all of Fed. Rep. of Germany

[73] Assignee: BASF Aktiengesellschaft, Ludwigshafen, Fed. Rep. of Germany

[21] Appl. No.: 948,347

[22] Filed: Oct. 4, 1978

[30] Foreign Application Priority Data

Oct. 8, 1977 [DE] Fed. Rep. of Germany ....... 2745449
Nov. 18, 1977 [DE] Fed. Rep. of Germany ....... 2751519

[51] Int. Cl.² ............................ C09B 29/00; D06P 1/18
[52] U.S. Cl. .......................................... 8/550; 8/583; 8/672
[58] Field of Search ................... 8/1 C, 1 W, 173, 174, 8/82, 83

[56] References Cited

U.S. PATENT DOCUMENTS

| | | | |
|---|---|---|---|
| 2,979,528 | 4/1961 | Lundsted | 260/574 |
| 3,781,169 | 12/1973 | Deubel et al. | 8/173 |
| 3,923,457 | 12/1975 | Ong et al. | 8/173 |
| 3,993,439 | 11/1976 | Deubel et al. | 8/173 |
| 4,058,480 | 11/1977 | Lohmann et al. | 8/79 |
| 4,072,465 | 2/1978 | Daeuble | 8/173 |
| 4,073,615 | 2/1978 | Lacroix et al. | 8/79 |
| 4,101,273 | 7/1978 | Matsuba et al. | 8/173 |
| 4,132,523 | 1/1979 | Ong | 8/173 |
| 4,137,251 | 1/1979 | Berger | 8/173 |

FOREIGN PATENT DOCUMENTS

2502839 5/1976 Fed. Rep. of Germany.
1449712 9/1976 United Kingdom.

*Primary Examiner*—Ronald W. Griffin
*Attorney, Agent, or Firm*—Oblon, Fisher, Spivak, McClelland & Maier

[57] ABSTRACT

The invention relates to an aqueous disperse dye or optical brightener formulation which comprises (a) from 5 to 55 percent by weight, based on (a+c), of one or more finely divided dyes, optical brighteners or mixtures of these, (b) from 10 to 200 percent by weight, based on (a), of a water-soluble surfactant of the formula

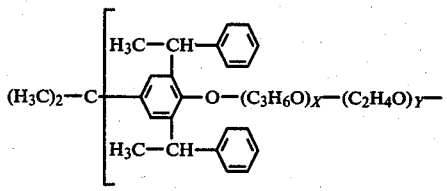

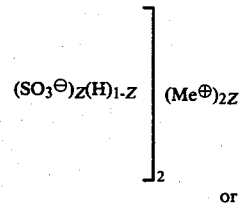

or

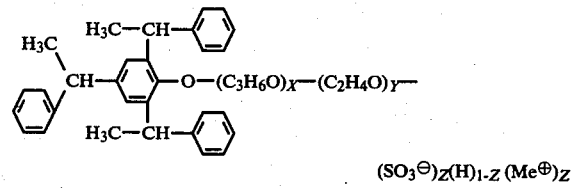

where X is from 0 to a mean value of 125, Y is from a mean value of 37 to a mean value of 250, but if X is >37, Y:X is at least 1:1, Z is 0 or 1 and Me⊕ is an alkali metal ion, or mixtures of such surfactants, (c) from 45 to 95 percent by weight, based on (a+c) of water or of a mixture of water and a water-retaining agent, with or without (d) further additives conventionally present in aqueous formulations.

8 Claims, No Drawings

STABLE FINELY DISPERSED AQUEOUS FORMULATIONS OF DISPERSE DYES AND OPTICAL BRIGHTENERS, AND THEIR USE

The present invention relates to stable finely dispersed aqueous formulations of disperse dyes or sparingly water-soluble, or water-insoluble, optical brighteners, which formulations are mobile and pourable, and to the use of such formulations.

As a result of the use of new and shorter dyeing methods, the required standards of finish of disperse dyes for synthetic fibers have risen substantially in recent years.

Package dyeing under HT conditions (from 120° to 135° C.) makes very particularly high demands on the fineness of dispersion, and the stability, of dye dispersions.

According to the prior art, perfectly level package dyeings, without dye filtration occurring during dyeing, are only achieved with formulations containing certain lignin-sulfonates. However, these ligninsulfonates are not effective with all dyes since the latter vary substantially in properties such as particle size, particle size distribution, hydrophilic character and—albeit slight—solubility in water.

A further disadvantage of the ligninsulfonates is that they soil polyester fibers severely during dyeing. This is particularly objectionable where light shades or brilliant hues are concerned.

In addition, these ligninsulfonates tend to reduce sensitive azo dyes during the dyeing process, ie. in such cases, greatly reduced color yields are obtained.

Particularly unfavorable behavior when used for package dyeing is exhibited by formulations containing dispersants from the following categories: naphthalenesulfonic acid/formaldehyde condensation products, condensation products of cresol, 2-naphthol-6-sulfonic acid, sodium sulfite and formaldehyde (FIAT Report 1013) and sulfomethylation products as described in German Laid-Open Applications DOS 2,032,926 and 2,301,638.

Satisfactory package dyeing is also not achievable with the non-ionic aqueous formulations described in German Pat. No. 2,502,839, since the non-ionic dispersants contained in these formulations have cloud points below 120° C. and hence the dispersions, on heating to 120° C. or above, undergo partial or complete flocculation.

According to the invention, there is provided an aqueous disperse dye or optical brightener formulation which formulation comprises
(a) from 5 to 55 percent by weight, based on (a+c), of one or more finely divided disperse dyes, one or more finely divided optical brighteners or a mixture of one or more finely divided disperse dyes with one or more finely divided optical brighteners,
(b) from 10 to 200 percent by weight, based on (a), of a water-soluble surfactant of one of the general formulae below:

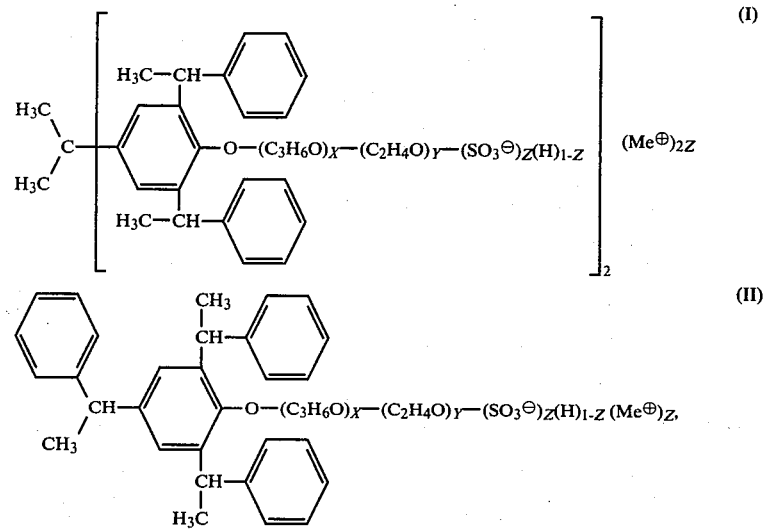

where X is 0 or has a mean value of 125, Y has a mean value of 37 to 250, with the proviso that if X is >37, the ratio Y:X is at least 1:1, Z independently is 0 or 1 and Me⊕ is an alkali metal ion, or a mixture of two or more such surfactants,
(c) from 45 to 95 percent by weight, based on (a+c), of water or of a mixture of water and a water-retaining agent, with or without
(d) further additives conventionally present in aqueous dye formulations.

The fluid aqueous formulations of the invention are dispersions of low viscosity, which remain stable, and retain their low viscosity, both on prolonged storage at from 25° to 30° C. and on several days' storage at 60° C. During storage, the fine dispersion of the dye or optical brightener particles remains virtually unchanged.

The novel formulations are outstandingly suitable for dyeing or optically brightening textile material containing synthetic fibers at up to 140° C., especially textile material of cellulose esters and very particularly textile material consisting of linear polyester fibers or of mixtures of such fibers with cellulose.

Using the novel formulations, dyebath formulations and optical brightener formulations are obtained in which the dye or optical brightener is in stable dispersion and does not undergo flocculation at up to 140° C., even in the presence of conventional dyeing assistants.

Examples of suitable disperse dyes (a) are sparingly water-soluble, or water-insoluble, dyes from the azo series, the anthraquinone series and the quinophthalone series, and dyes from other categories of compounds which are sparingly water-soluble, or water-insoluble, and are absorbed on synthetic fibers from an aqueous liquor, as well as sparingly water-soluble, or water-insoluble, optical brighteners, or mixtures of such dyes and/or optical brighteners.

The content of (a) is from 5 to 55, preferably from 10 to 30, percent by weight, based on (a+b).

The water-soluble surfactants (b) can be obtained by reacting phenol derivatives of the formulae:

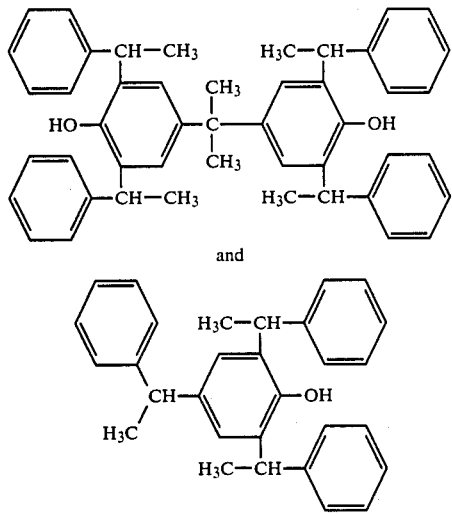

with propylene oxide, followed by reaction of the adduct with ethylene oxide, or, if X=0, by reacting (III) and/or (IV) with ethylene oxide. The adducts may or may not be reacted, completely or partially, with chlorosulfonic acid or sulfur trioxide to give sulfuric acid half-esters, which can be neutralized with alkalis.

The phenols of the formulae III and IV can be obtained in the conventional manner by reacting phenol or 2,2-(p,p'-bis-hydroxydiphenyl)-propane with, respectively, 3 or 4 moles of styrene, in the presence of an acid catalyst.

The phenols III and IV can be reacted by conventional methods first with propylene oxide and then with ethylene oxide, or only with ethylene oxide, in the presence of acid or alkaline catalysts, to give the corresponding oxyalkylation products (I) and (II), where Z=0. For example, the oxyalkylation may be carried out by the method described in U.S. Pat. No. 2,979,528.

The sulfuric acid half-esters can be prepared by reacting the oxyalkylation products with chlorosulfonic acid or with sulfur trioxide, the amount being selected so as to react (sulfate) either all the free hydroxyl groups or only a part thereof. In the latter case, mixtures of compounds of the formulae I and II, containing free hydroxyl groups and sulfated hydroxyl groups, are formed. For use as surfactants, the sulfuric acid half-esters obtained from the reaction are converted to alkali metal salts, for example the sodium salts or potassium salts (Me⊕=Na⊕ or K⊕). In the case of chlorosulfonic acid, two equivalents and in the case of sulfur trioxide one equivalent of basic compound is required. The basic compound used is advantageously an aqueous alkali metal hydroxide. The temperature during neutralization should in general not exceed 70° C. The salts obtained can be used in the form of aqueous solutions or can be isolated as such and used as solids.

The required amount of (b) depends on the one hand on the dye (a) to be dispersed and on its concentration in the formulation, and on the other hand on the nature of the agent (b). With dyes which are difficult to disperse or flocculate easily, larger amounts of (b) are used than with dyes which are easily dispersible and/or have little tendency to flocculate. The minimum amount of (b) is 10 percent by weight based on (a). In general, from 30 to 200 percent by weight, preferably from 50 to 100 percent by weight—based on (a)—of surfactant (b) are employed.

For technological reasons, formulations containing surfactants (b) where X is from 0 to a mean value of 2.5, Y has a mean value of from 37 to 250 and Z is from 0 to a mean value of 0.5, are preferred. Formulations containing agents (b) where X is from 0 to a mean value of 2.5, Y has a mean value of from 50 to 100 and Z has a mean value of 0.5 are more especially preferred. Constituent (c) is water or, preferably, a mixture of water and a water-retaining agent; the latter is intended to prevent drying-up and encrusting of the fluid formulation. Examples of water-retaining agents are glycols, diglycols and triglycols, eg. ethylene glycol, diethylene glycol, triethylene glycol, propylene glycol, dipropylene glycol, tripropylene glycol, 1,2-butylene glycol, glycerol or mixtures of two or more of these.

Examples of additives (d) conventionally used in aqueous dispersions are disinfectants, eg. mold preventatives, and pH regulators, eg. buffers and/or alkalis or acids used to bring the aqueous phase of the dispersion to a particular pH. The amount of these additives may be up to 2.5 percent by weight, based on the formulation (=a+b+c+d).

The aqueous formulations of the invention can be prepared in the conventional manner by dispersing or homogenizing the disperse dye (a) in the presence of the water-soluble surfactant (b) and of the agent (c). The disperse dyes and optical brighteners may be used as powders or, preferably, as the press cake obtained from their process of manufacture.

Dispersion can be carried out in conventional comminution machinery, eg. kneaders, ball mills, dispersers, sand mills, bead mills or attrition mills. Dispersion is terminated when the disperse dye/optical brightener has reached the desired state of fine dispersion. Thereafter, the formulation can be adjusted to the desired tinctorial strength.

The formulations of the invention are illustrated by the Examples which follow. Unless stated otherwise, parts and percentages are by weight.

The state of fine dispersion of the formulations is characterized by the centrifugal sedimentation values obtained from a centrifuging test (Richter and Vescia, Melliand Textilberichte, 1965, No. 6, 622).

A. PREPARATION OF THE SURFACTANTS (B)

(al) Preparation of the phenol derivative III 312 g of styrene are introduced into a 4 liter round-bottomed flask equipped with a stirrer, dropping funnel, thermometer and reflux condenser, and are heated to 50° C. At this temperature, 684 g of 2,2-(p,p'-dihydroxydiphenyl)-propane are introduced and 9.7 g of anhydrous p-toluenesulfonic acid are added to the suspension. After a short time, an exothermic reaction occurs, and the temperature of the reaction solution rises to about 120°–140° C. A clear oil results. In the course of 3 hours, a further 936 g of styrene are added to this reaction mixture at 120°–140° C. To complete the reaction the mixture is stirred for a further hour at this temperature. The product, which is very viscous at room temperature, is packaged at 70°-90° C. It is reddish brown in color.

(a2) Preparation of the phenol derivative (IV)

94 g of phenol are fused, 2.03 g of p-toluenesulfonic acid are added as a catalyst, and 312 g of styrene are added dropwise in the course of 4 hours at 130° C., whilst stirring. The reaction mixture is then kept at 130° C. for 4 hours.

(b) Oxyalkylation of the phenol derivatives obtained according to (a1) and (a2).

(b1) 1,896 g (=3 moles) of the reaction product obtained as described in (a1) and 19 g of potassium hydroxide powder are introduced into an autoclave and 870 g (=15 moles) of propylene oxide are introduced in portions at 120° C., whilst stirring, under such conditions that the pressure does not rise above 3 bar.

13,200 g (=300 moles) of ethylene oxide are then introduced at the same temperature, in the same manner.

The reaction product is discharged from the autoclave whilst warm and solidifies, on cooling, to a colorless mass of melting point about 52° C.

(b2) 1,896 g (=3 moles) of the product prepared as described in (a1) are mixed in an autoclave with 19 g of potassium hydroxide powder and 13,200 g (=300 moles) of ethylene oxide are introduced in portions at 120° C., whilst stirring, under conditions such that the pressure does not rise above 3 bar.

The oxyethylation product (15,115 g) is run out whilst warm and solidifies to a colorless mass of melting point about 50° C.

(c) Preparation of the sulfuric acid half-ester 15,115 g (=3 moles) of the ethylene oxide adduct obtained as described in (b2) are fused, the melt is cooled to 50°-60° C. and at this temperature 349.5 g of chlorosulfonic acid are added dropwise in the course of 10 minutes. To complete the reaction, the mixture is stirred for a further 30 minutes at 50°-70° C.

The reaction mixture is then neutralized with aqueous sodium hydroxide solution of about 50 percent strength at below 70° C. (pH 6-7). The product can be poured out at 60°-70° C. and solidifies on cooling. Melting point about 50° C. Yield, 15,428 g of actual surfactant.

The reaction can also be carried out in the same way with sulfur trioxide.

Other water-soluble surfactants (b) were prepared by a similar method. They are listed in Tables A1 and A2.

The surfactants (b) are characterized by the phenol on which they are based, the amount of propylene oxide and ethylene oxide used to form the adduct per mole of phenol, and the amount of chlorosulfonic acid used per mole of adduct.

TABLE A 1

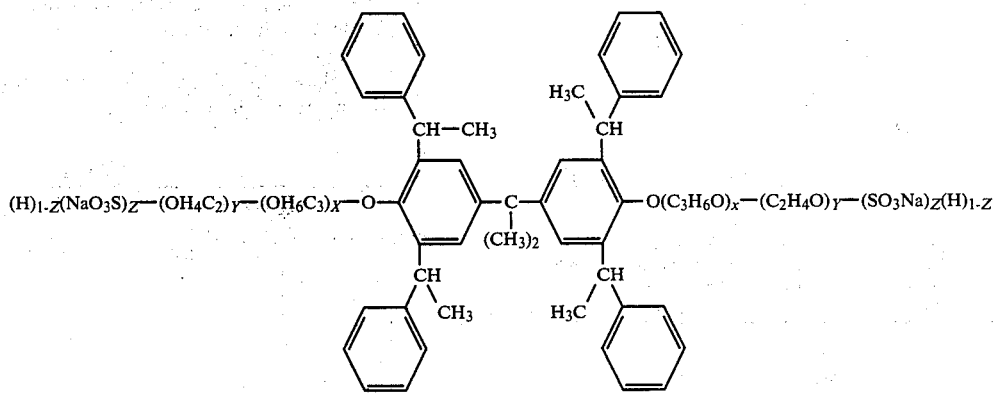

| Water-soluble surfactant No. | Moles of propylene oxide/ mole of phenol | $\overline{X}$ | Moles of ethylene oxide/ moles of phenol or adduct | $\overline{Y}$ | Moles of chlorosulfonic acid/ mole of adduct | $\overline{Z}$ |
|---|---|---|---|---|---|---|
| 1 | 0 | 0 | 75 | 37.5 | 0 | 0 |
| 2 | 0 | 0 | 100 | 50 | 0 | 0 |
| 3 | 0 | 0 | 125 | 62.5 | 0 | 0 |
| 4 | 0 | 0 | 150 | 75 | 0 | 0 |
| 5 | 0 | 0 | 200 | 100 | 0 | 0 |
| 6 | 0 | 0 | 300 | 150 | 0 | 0 |
| 7 | 0 | 0 | 500 | 250 | 0 | 0 |
| 8 | 5 | 2.5 | 100 | 50 | 0 | 0 |
| 9 | 100 | 50 | 150 | 75 | 0 | 0 |
| 10 | 100 | 50 | 200 | 100 | 0 | 0 |
| 11 | 200 | 100 | 250 | 125 | 0 | 0 |
| 12 | 0 | 0 | 75 | 37.5 | 2 | 1.0 |
| 13 | 0 | 0 | 100 | 50 | 1 | 0.5 |
| 14 | 0 | 0 | 200 | 100 | 1 | 0.5 |
| 15 | 0 | 0 | 125 | 62.5 | 2 | 1.0 |
| 16 | 0 | 0 | 300 | 150 | 1 | 0.5 |
| 17 | 0 | 0 | 500 | 250 | 1 | 0.5 |
| 18 | 5 | 2.5 | 150 | 75 | 2 | 1.0 |
| 19 | 100 | 50 | 100 | 50 | 2 | 1.0 |
| 20 | 100 | 50 | 150 | 75 | 2 | 1.0 |
| 21 | 100 | 50 | 200 | 100 | 2 | 1.0 |

TABLE A 1-continued

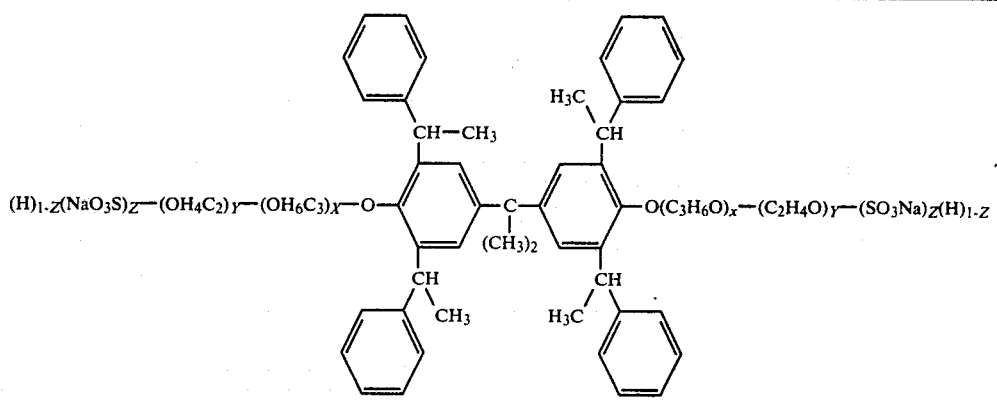

| Water-soluble surfactant No. | Moles of propylene oxide/ mole of phenol | Amount used to form the adduct | | | Moles of chlorosulfonic acid/ mole of adduct | |
|---|---|---|---|---|---|---|
| | | X | Moles of ethylene oxide/ moles of phenol or adduct | Y | | Z |
| 22 | 200 | 100 | 250 | 125 | 2 | 1.0 |
| 23 | 1.0 | 0.5 | 100 | 50.0 | 1 | 0.5 |
| 24 | 2.0 | 1.0 | 100 | 50 | 1 | 0.5 |

TABLE A 2

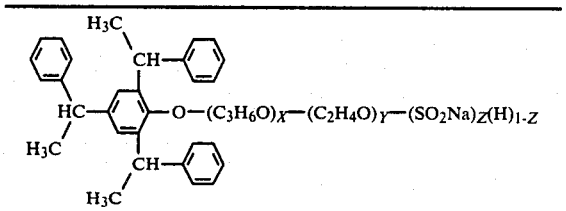

| Water-soluble surfactant No. | X = moles of propylene oxide/mole of phenol | Y = moles of ethylene oxide/mole of adduct or phenol | Z = moles of chlorosulfonic acid/mole of adduct |
|---|---|---|---|
| 25 | 0 | 100 | 0 |
| 26 | 50 | 100 | 0 |
| 27 | 100 | 100 | 0 |
| 28 | 100 | 200 | 0 |
| 29 | 0 | 100 | 1 |
| 30 | 50 | 100 | 1 |
| 31 | 100 | 100 | 1 |
| 32 | 100 | 200 | 1 |
| 33 | 10 | 100 | 1 |
| 34 | 2.5 | 100 | 1 |

B. Dye formulations

EXAMPLES 1 TO 30

11 parts of the dye of the formula

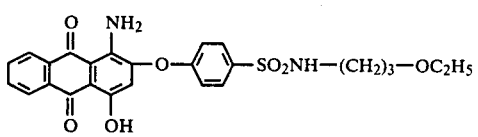

in the form of its aqueous press cake are milled with 11 parts of one of the surfactants listed in Tables A 1 and A 2, 10 parts of ethylene glycol and 68 parts of water until the particle size is less than 1 μm. The milling time and the milling equipment used are shown in Table I. The formulations exhibit a good state of dispersion, as characterized by the centrifugal sedimentation values in Table I. The formulations are mobile, and stable on storage.

Packages dyed with the formulations exhibit level dyeing throughout the cheese, without any dye filtration.

TABLE I

| Example | Surfactant No. | Milling equipment | Milling time | Centrifugal sedimentation values |
|---|---|---|---|---|
| 1 | 1 | Ball mill | 200 h. | 4, 7, 24, 65 |
| 2 | 2 | " | " | 2, 7, 15, 76 |
| 3 | 3 | " | " | 3, 12, 28, 57 |
| 4 | 4 | " | " | 2, 8, 31, 59 |
| 5 | 5 | Sand mill | 4 Passes | 2, 7, 22, 69 |
| 6 | 6 | " | " | 6, 17, 39, 38 |
| 7 | 7 | " | " | 3, 14, 32, 51 |
| 8 | 8 | " | " | 6, 24, 42, 28 |
| 9 | 9 | " | " | 2, 4, 27, 67 |
| 10 | 10 | Bead mill | 24 h. | 2, 8, 27, 63 |
| 11 | 11 | " | " | 1, 5, 35, 59 |
| 12 | 12 | " | " | 1, 12, 40, 47 |
| 13 | 13 | " | " | 2, 6, 20, 72 |
| 14 | 14 | " | " | 7, 8, 36, 49 |
| 15 | 15 | " | " | 3, 20, 41, 36 |
| 16 | 16 | " | " | 4, 13, 29, 54 |
| 17 | 17 | " | " | 3, 12, 30, 55 |
| 18 | 18 | Attrition mill | 30 h. | 4, 16, 36, 44 |
| 19 | 19 | " | " | 1, 6, 27, 66 |
| 20 | 20 | " | " | 2, 4, 23, 71 |
| 21 | 21 | " | " | 3, 12, 32, 53 |
| 22 | " | " | | 1, 7, 26, 77 |
| 23 | 23 | " | " | 2, 3, 3, 92 |
| 24 | 24 | " | " | 4, 13, 35, 48 |
| 25 | 25 | " | " | 13, 38, 34, 15 |
| 26 | 26 | " | " | 2, 11, 40, 47 |
| 27 | 27 | " | " | 2, 2, 18, 78 |
| 28 | 28 | " | " | 4, 6, 23, 67 |
| 29 | 29 | " | " | 1, 5, 26, 68 |
| 30 | 30 | " | " | 1, 5, 17, 77 |

EXAMPLES 31 TO 50

18 parts of the dye of the formula

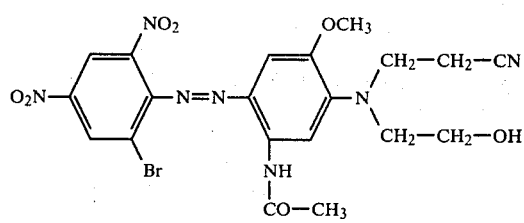

in the form of its aqueous press cake are milled with 9 parts of one of the surfactants shown in Table II, 10 parts of ethylene glycol and 63 parts of water until the particle size is less than 1 μm. The dispersions obtained are mobile and stable on storage, and give level dyeings when used for package dyeing of texturized polyester.

The formulations exhibit a good state of dispersion, as shown by the centrifugal sedimentation values in Table II.

TABLE II

| Example | Surfactant No. | Milling equipment | Milling time | Centrifugal sedimentation values |
|---|---|---|---|---|
| 31 | 1 | Bead mill | 24 h. | 8, 26, 38, 28 |
| 32 | 2 | " | " | 5, 19, 33, 43 |
| 33 | 5 | " | " | 11, 29, 33, 27 |
| 34 | 6 | " | " | 10, 19, 33, 38 |
| 35 | 7 | " | " | 11, 29, 37, 23 |
| 36 | 9 | " | " | 6, 21, 35, 38 |
| 37 | 10 | Attrition mill | 30 h. | 2, 20, 38, 40 |
| 38 | 11 | " | " | 3, 22, 35, 40 |
| 39 | 13 | " | " | 1, 10, 31, 58 |
| 40 | 16 | " | " | 8, 32, 37, 18 |
| 41 | 17 | " | " | 9, 39, 34, 18 |
| 42 | 19 | " | " | 1, 5, 19, 75 |
| 43 | 20 | " | " | 1, 5, 14, 80 |
| 44 | 21 | " | " | 2, 12, 26, 60 |
| 45 | 22 | " | " | 2, 7, 31, 60 |
| 46 | 24 | " | " | 3, 16, 39, 42 |
| 47 | 25 | " | " | 6, 23, 31, 40 |
| 48 | 26 | " | " | 3, 23, 37, 37 |
| 49 | 29 | " | " | 4, 9, 29, 58 |
| 50 | 30 | " | " | 8, 14, 35, 43 |

EXAMPLES 51 TO 55

12.5 parts of the optical brightener of the formula

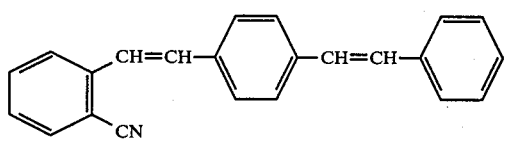

in the form of an aqueous press cake are milled with 18 parts of one of the surfactants shown in Table III, 15 parts of ethylene glycol, 4 parts of triethanolamine and 50.5 parts of water, in the milling equipment shown in Table III, until the particle size is less than 1 μm.

The aqueous formulations exhibit a good state of dispersion, as shown by the centrifugal sedimentation values in Table III. The formulations are mobile and stable on storage. Package dyeing gives packages with level brightening, without filtration.

Using the thermosol process, very good white effects are obtained; an afterwash is not necessary.

TABLE III

| Example | Surfactant No. | Milling equipment | Milling time | Centrifugal sedimentation values |
|---|---|---|---|---|
| 51 | 9 | Sand mill | 15 Passes | 13, 36, 42, 9 |

TABLE III-continued

| Example | Surfactant No. | Milling equipment | Milling time | Centrifugal sedimentation values |
|---|---|---|---|---|
| 52 | 13 | " | " | 6, 19, 44, 31 |
| 53 | 16 | Bead mill | 10 h. | 8, 40, 25, 27 |
| 54 | 22 | " | " | 6, 14, 32, 48 |
| 55 | 30 | " | " | 11, 20, 38, 31 |

EXAMPLES 56 TO 61

25 parts of the dye of the formula

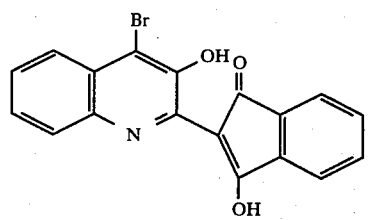

in the form of an aqueous press cake are milled with 12.5 parts of one of the surfactants shown in Table IV, 15 parts of ethylene glycol and 47.5 parts of water, in the milling equipment shown in Table IV, until the particle size is less than 1 μm.

The formulations exhibit a good state of dispersion, as shown by the centrifugal sedimentation values in Table IV.

TABLE IV

| Example | surfactant No. | Milling equipment | Milling time | Centrifugal sedimentation values |
|---|---|---|---|---|
| 56 | 23 | Bead mill | 15 h. | 9, 21, 37, 33 |
| 57 | 24 | " | " | 11, 19, 35, 35 |
| 58 | 33 | " | " | 8, 18, 34, 40 |
| 59 | 34 | " | " | 10, 21, 36, 33 |
| 60 | 10 | Sand mill | 12 Passes | 8, 17, 33, 42 |
| 61 | 13 | " | 15 Passes | 9, 19, 35, 37 |

We claim:

1. A stable finely dispersed aqueous formulation of disperse dyes and optical brighteners, which contains (a) from 5 to 55 percent by weight based on (a+c), of one or more finely divided disperse dyes, optical brighteners or mixtures of these, (b) from 10 to 200 percent by weight, based on (a), of a water-soluble surfactant of the general formula

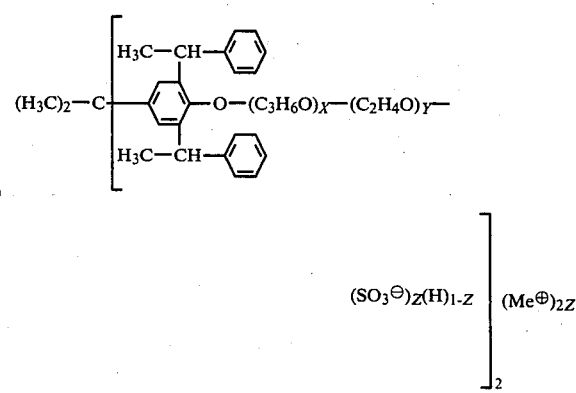

or

-continued

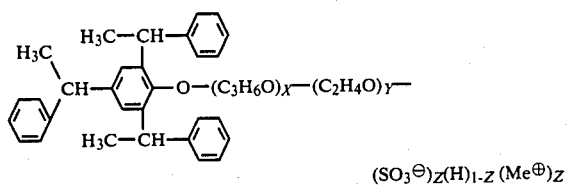

$$(SO_3^\ominus)_Z(H)_{1-Z}(Me^\oplus)_Z$$

where X is from 0 to a mean value of 125, Y is from a mean value of 37 to a mean value of 250, but if X is >37, Y:X is at least 1:1, Z is 0 or 1 and $Me^\oplus$ is an alkali metal ion, or mixtures of such surfactants, (c) from 45 to 95 percent by weight, based on (a+c) of water or of a mixture of water and water-retaining agent, and (d) from 0 to 2.5 percent by weight, based on the formulations, of a disinfectant, pH regulator or mixture thereof.

2. The formulation as claimed in claim 1, wherein, in surfactant (b), X is from 0 to a mean value of 2.5, Y has a mean value of from 37 to 250, and Z is from 0 to a mean value of 0.5.

3. The formulation as claimed in claim 1, wherein, in surfactant (b), X is from 0 to a mean value of 2.5, Y has a mean value of from 50 to 100, and Z has a mean value of 0.5.

4. The formulation as claimed in any of claims 1 to 3, which contains, based on (a+c), from 10 to 30 percent by weight of (a).

5. The formulation as claimed in claim 1, 2 or 3 which contains, based on (a), from 50 to 100 percent by weight of (b).

6. The formulation as claimed in claim 1, wherein the water-retaining agent is ethylene glycol, diethylene glycol, triethylene glycol, propylene glycol, dipropylene glycol, tripropylene glycol, 1,2-butylene glycol, glycerol or a mixture of these.

7. The formulation as claimed in claim 2 or 3, wherein the water-retaining agent is ethylene glycol, diethylene glycol, triethylene glycol, propylene glycol, dipropylene glycol, tripropylene glycol, 1,2-butylene glycol, glycerol or a mixture of these.

8. The formulation as claimed in claim 1, wherein the surfactant (b) is in the form of the potassium salt, the sodium salt or a mixture of both salts.

* * * * *